(12) United States Patent
Perryman et al.

(10) Patent No.: US 10,245,435 B1
(45) Date of Patent: Apr. 2, 2019

(54) WIRELESS NEURAL STIMULATOR IMPLANTATION

(71) Applicant: Micron Devices LLC, Miami Beach, FL (US)

(72) Inventors: Laura Tyler Perryman, Miami Beach, FL (US); Benjamin Speck, Miami Beach, FL (US)

(73) Assignee: Stimwave Technologies Incorporated, Pompano Beach, FL (US)

( * ) Notice: Subject to any disclaimer, the term of this patent is extended or adjusted under 35 U.S.C. 154(b) by 255 days.

(21) Appl. No.: 14/590,524

(22) Filed: Jan. 6, 2015

Related U.S. Application Data

(60) Provisional application No. 61/923,792, filed on Jan. 6, 2014.

(51) Int. Cl.
| | | |
|---|---|---|
| *A61B 19/00* | (2006.01) | |
| *A61N 1/375* | (2006.01) | |
| *A61N 1/36* | (2006.01) | |
| *A61N 1/372* | (2006.01) | |
| *A61M 25/06* | (2006.01) | |
| *A61N 1/05* | (2006.01) | |

(52) U.S. Cl.
CPC ........ *A61N 1/3756* (2013.01); *A61B 19/5244* (2013.01); *A61M 25/0606* (2013.01); *A61N 1/36071* (2013.01); *A61N 1/37229* (2013.01); *A61B 2019/5238* (2013.01); *A61B 2019/5276* (2013.01); *A61N 1/0551* (2013.01)

(58) Field of Classification Search
CPC ............. A61N 1/3756; A61M 25/0606; A61B 19/5244
See application file for complete search history.

(56) References Cited

U.S. PATENT DOCUMENTS

| | | | | |
|---|---|---|---|---|
| 5,876,408 A | * | 3/1999 | Alt ......................... | A61N 1/056 606/129 |
| 2007/0276362 A1 | * | 11/2007 | Rioux ................ | A61B 18/1492 606/41 |
| 2012/0209283 A1 | * | 8/2012 | Zhu ...................... | A61N 1/0553 606/129 |

FOREIGN PATENT DOCUMENTS

WO    WO 2012138782 A1 * 10/2012    ........... A61N 1/0551

* cited by examiner

*Primary Examiner* — Gregory Anderson
(74) *Attorney, Agent, or Firm* — Fish & Richardson P.C.

(57) ABSTRACT

Some implementations provide a method for implanting a neurostimulator system that includes: placing an introducer through an incision site on a patient into an epidural space of the patient, the introducer including a sheath and the patient having a primary area of pain; placing a neurostimulator system through the introducer into the epidural space of the patient, the neurostimulator system comprising an enclosure housing at least one pair of electrodes and at least one passive antenna; advancing the neurostimulator system through the epidural space such that the electrodes are placed at a targeted tissue of the patient; removing the introducer sheath from the epidural space of the patient; adjusting the neurostimulator system enclosure to leave a customized length of the device body enclosure in the epidural space; and anchoring the customized length of the neurostimulator system enclosure in tissue of the patient.

21 Claims, 15 Drawing Sheets

WIRELESS NEURAL STIMULATOR IMPLANTATION

CROSS REFERENCE TO RELATED APPLICATIONS

This application claims benefit of U.S. provisional Patent Application 61/923,792, filed Jan. 6, 2014, the contents of which are hereby incorporated by reference in their entirety.

TECHNICAL FIELD

This description is related to implanting a neural stimulator.

BACKGROUND

In general, an implantable neural stimulator can be placed near neural tissue and generate an electrical stimulation signal that is used to inhibit nervous system activity. Some implantable neural stimulators have a circular cross-sectional shape and include conductive ring shaped contacts spaced apart from each other at the distal end of the body, with the contacts operating as individual electrodes. A programmer is used to configure parameters of the stimulation signal for the specific patient's therapy.

SUMMARY

In one aspect, some implementations provide a method for implanting a neurostimulator system. The method includes: placing an introducer through an incision site on a patient into an epidural space of the patient, the introducer including a sheath; placing a neurostimulator system through the introducer into the epidural space of the patient, the neurostimulator system comprising an enclosure housing at least one pair of electrodes and at least one passive antenna, the at least one passive antenna configured to receive, via electric radiative coupling, electrical energy and waveform parameters from an antenna placed exterior to the patient; advancing the neurostimulator system through the epidural space such that the electrodes are placed at a targeted tissue of the patient capable of receiving therapy through electrical waveforms applied at the electrodes, the electrical waveforms generated based on the received electrical energy and waveform parameters; removing the introducer sheath from the epidural space of the patient; adjusting the neurostimulator system enclosure to leave a customized length of the device body enclosure in the epidural space; and anchoring the customized length of the neurostimulator system enclosure in tissue of the patient.

Implementations may include one or more of the following features. Adjusting the neurostimulator system enclosure may include: cutting the neurostimulator system enclosure such that the customized length fits between the incision site on the patient and the targeted tissue of the patient. Adjusting the neurostimulator system enclosure also may include: adjusting a placement of the neurostimulator system enclosure such that relief provided by the electrodes covers an area that substantially overlaps the primary treatment area for the patient. The method may additionally include: adjusting the waveform parameters to improve the relief provided by the electrodes of the neurostimulator system.

The method may further include: placing an additional neurostimulator system through the introducer sheath in to the epidural space of the patient, the additional neurostimulator system comprising an enclosure housing at least one pair of electrodes and at least one passive antenna, the at least one passive antenna configured to receive, via electric radiative coupling, electrical energy and waveform parameters from the antenna placed exterior to the patient. The method may further include: advancing the additional neurostimulator system through the epidural space to enhance the therapy. Advancing the additional neurostimulator system through the epidural space may include: advancing the additional neurostimulator system through the epidural space such that the electrodes of the additional neurostimulator system are placed near the targeted tissue of the patient to enhance the therapy.

The method may further include using X-Ray fluoroscopy to guide placing the neurostimulator system through the introducer sheath into the epidural space. The method may further include: using X-Ray fluoroscopy to guide advancing the neurostimulator system through the epidural space. The method may further include: using ultrasound sonography to guide placing the neurostimulator system through the introducer sheath into the epidural space. The method may further include: using ultrasound sonography to guide advancing the neurostimulator system through the epidural space. The method may further comprising: attaching a radiopaque marker to the customized length of the enclosure in the epidural space of the patient. The method may further include: using fluoroscopy to locate the radiopaque marker before explanting the anchored neurostimulator system. The method may further include: using ultrasound sonography to locate the radiopaque marker before explanting the anchored neurostimulator system.

Placing the introducer sheath may further include: placing the introducer sheath along with an introducer needle-stylet assembly. The method may further include: removing the needle stylet from the assembly while leaving the introducer sheath in the epidural space. The method may further includes: placing a guide wire through the introducer sheath and advancing the guide wire into the epidural space. The method may further include: advancing the guide wire to no more than approximately 3 cm past a tip of the introducer sheath. The method may further include advancing the neurostimulator system by gliding the neurostimulator system within the introducer sheath and into the epidural space.

Anchoring the customized length of the enclosure further comprises: using suture to secure the customized length of the enclosure to a connective tissue at the incision site.

The details of one or more implementations are set forth in the accompanying drawings and the description below. Other features, objects, and advantages will be apparent from the description and drawings, and from the claims.

DETAILED DESCRIPTION

The disclosure herein describes some examples of procedures for placing a passive neurostimulator system through an introducer into the epidural space to provide stimulation to tissue, for example, in need of pain-relief therapy. The implantation procedure is minimally invasive and without extensive surgery. Thus, side effects may be reduced. Through electric radiative coupling, the passive neurostimulator system receives electric energy and waveform parameters from an antenna of an external pulse generator placed outside the patient's body. The passive neurostimulator system includes no active power source or components for inductive coupling to an external pulse generator. Thus, the implantable neurostimulator system can be compact, the length of which can be adjustable during a placement procedure. In fact, some placement procedures disclosed herein may allow the clinician to (i) advance the neurostimulator system to a point where the electrodes of the device provide a substantially optimized treatment for pain-relief, as determined during the placement procedure; and then (ii) cut the device at the incision entry point to fit the length of the neurostimulator system to the target location of the tissue to receive the substantially optimized pain-relief treatment. In contrast, neurostimulator devices that are fixed in length are less advantageous because these fixed-length stimulator devices cannot be adjusted in length during placement procedures. Additionally, the placement procedure disclosed herein may include adding a radiopaque plug to the implantable neurostimulator system to provide a mark on radiographic images. The mark may flag to a treating clinician the location of the implantable neurostimulator system. The flagged location can guide the treating clinician during, for example, an explant procedure.

Figure 1:
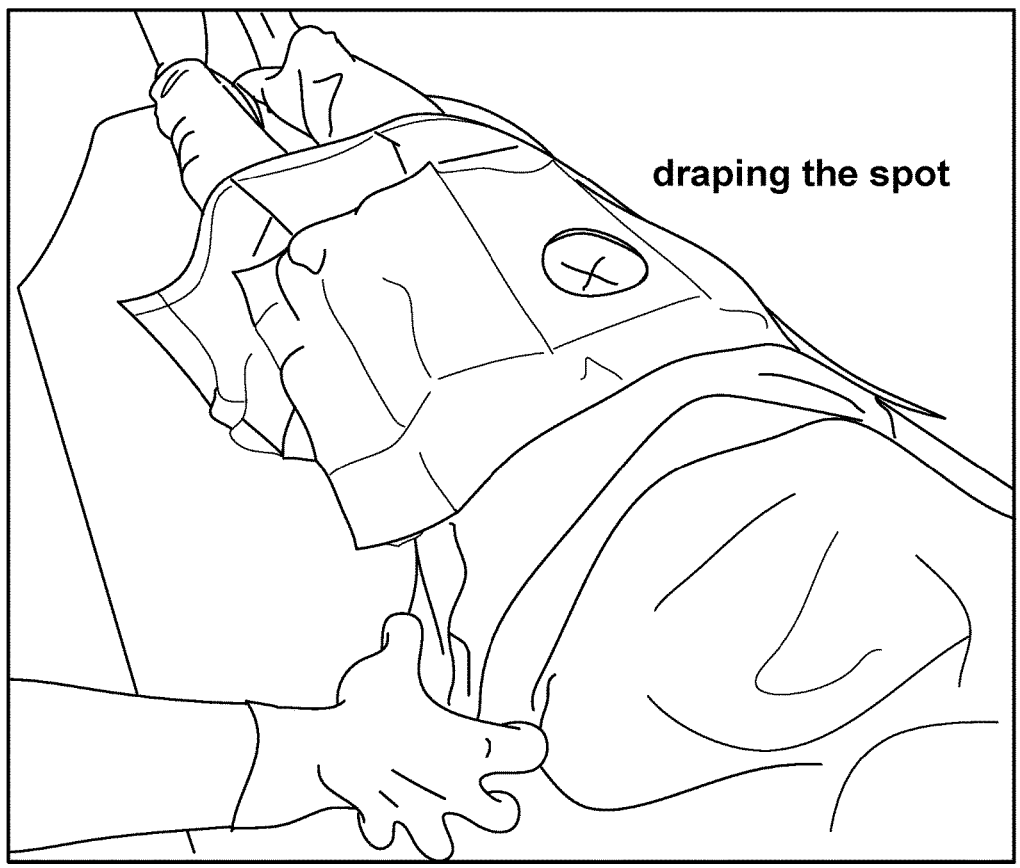
FIG. 1 depicts the method of draping the patient and marking the entry location for a needle-introducer assembly.

FIG. 1 depicts the method of draping the patient in the sterile environment and marking the entry location for the needle introducer. Thereafter, the device may be placed by making an incision at the needle-entry site to a depth of the subcutaneous fascia. Thus, the draping step may form a preparatory stage of an implantation or explantation procedure.

During an implantation procedure, a paramedian approach lateral to the midline may be used to insert the introducer sheath and needle stylet assembly into the epidural space at a shallow angle until resistance is encountered from the ligamentum flavum. A fluoroscope or other imaging technology, such as ultrasound sonography, may be used to visualize the location of the introducer sheath and needle assembly during the incision procedure.

Figure 2A:
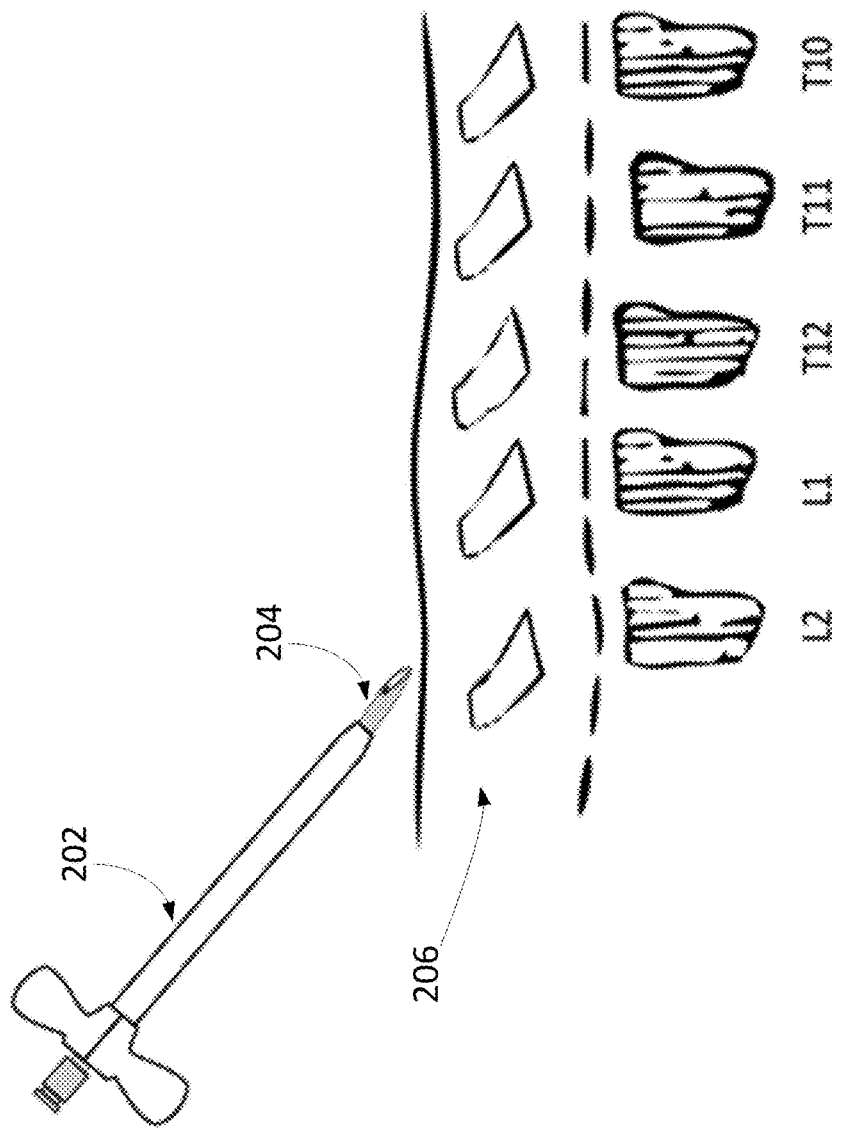
FIGS. 2A through 2H depict the steps for placing an implantable neural stimulator through an introducer to provide therapy to the patient.

At the physical location skin mark identified, the introducer sheath 202 and needle assembly 204 may be placed into the epidural space 206 at the L2-L1 vertebrae entry site, as illustrated in FIG. 2A. Needle assembly 204 may also be known as needle stylet assembly 204. The placement may be guided by fluoroscopy, including X-Ray and ultrasound, to verify that the introducer sheath and needle location are in the correct position.

Figure 2B:
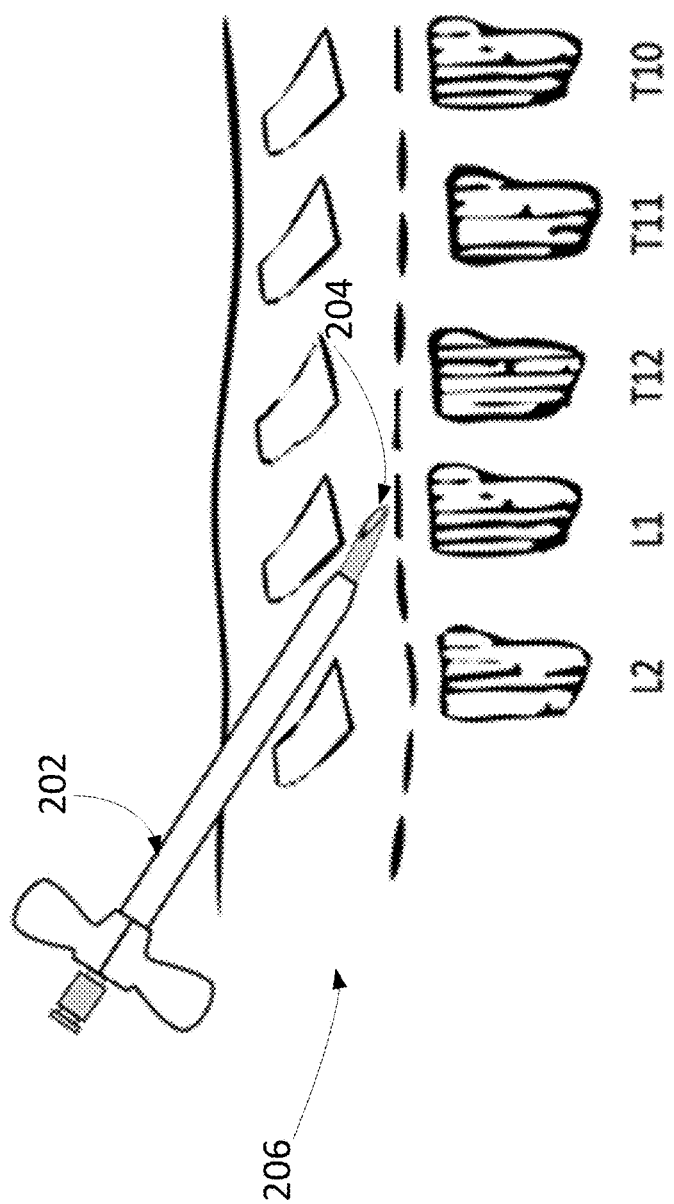

Subsequently, the introducer sheath 202 and needle assembly 204 may be rotated so that the beveled edge faces cephalad, as shown in FIG. 2B. The entry into the epidural space 206 may be confirmed by the loss-of-resistance technique with air or sterile water. The loss-of-resistance technique may often be used to identify the epidural space. Along with a sudden loss of resistance to pressure on the plunger of the syringe, a slight clicking sensation may be felt by the operator as the tip of the needle breaches the ligamentum flavum and enters the epidural space. Practitioners may use air or sterile water (e.g., saline) for identifying the epidural space. However, saline may be preferable to air, as saline associated with a better quality of analgesia and lower incidence of post-dural-puncture headache.

Figure 2C:
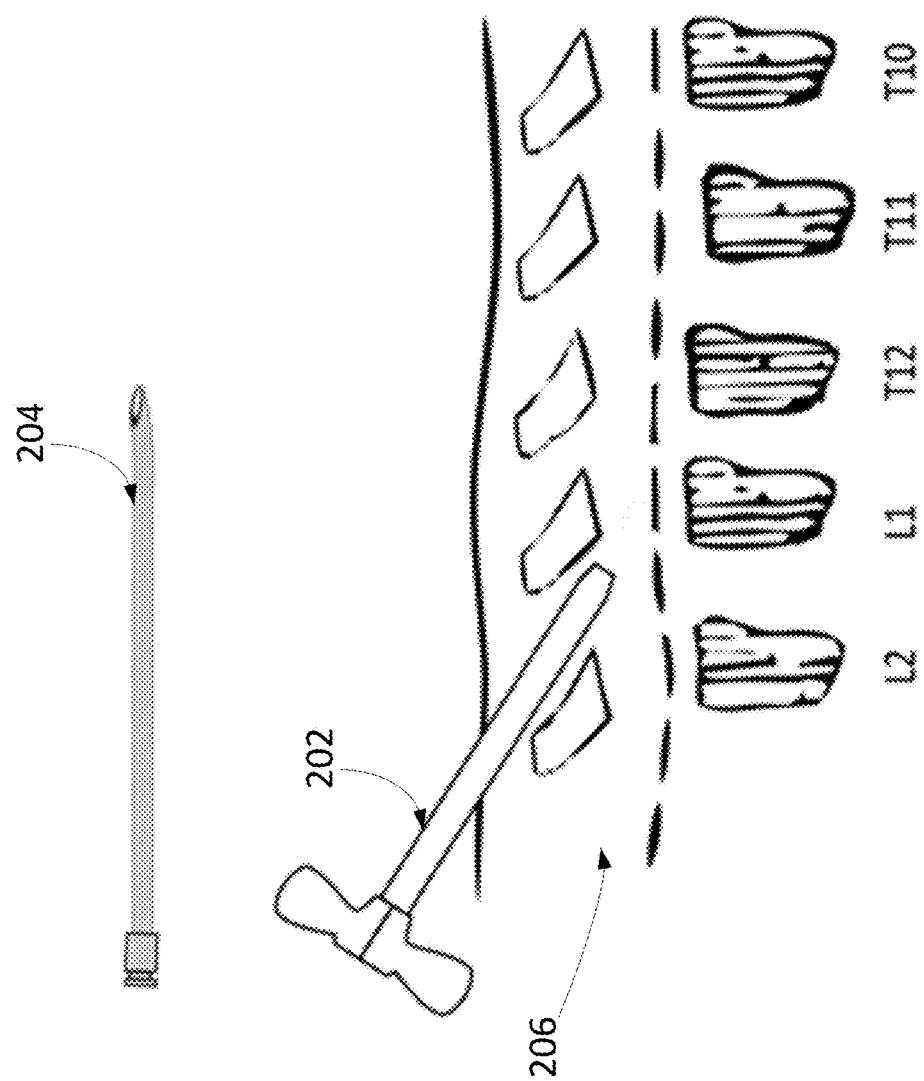

When the introducer sheath 202 and needle stylet assembly 204 has entered the epidural space, the metal needle may block the energy from the external transmitter and thus may be removed before intraoperative stimulation. On the other hand, the introducer sheath 202 is RF transparent and can be used throughout intraoperative testing. The needle stylet 204 may be removed, as shown in FIG. 2C. In some implementations, the introducer sheath position may be maintained with the operator physically holding the exposed portion by hand. In one configuration, when the needle stylet 204 has been removed from the assembly with the introducer sheath position maintained, a guide wire may then be inserted through the introducer sheath. The guide wire may then be advanced to a position no further than 1-3 cm past the tip of the introducer sheath.

Figure 2D:
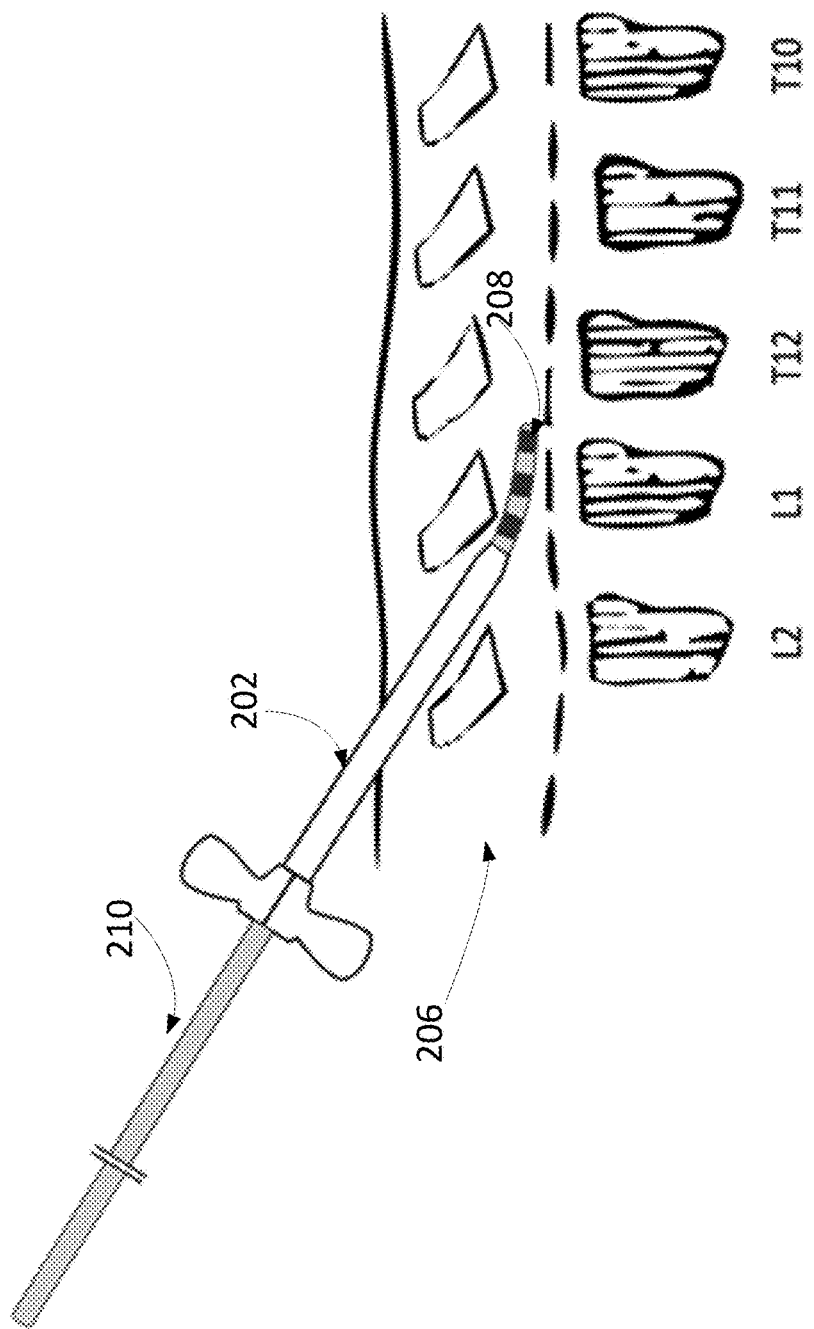

The guide wire is removed from the introducer sheath and replaced with the neural stimulator device 210, also referred to as neurostimulator system 210. The placement and advancement of the neural stimulator device 210 may be guided by fluoroscopy, as described above. as shown in FIG. 2D.

Figure 4:
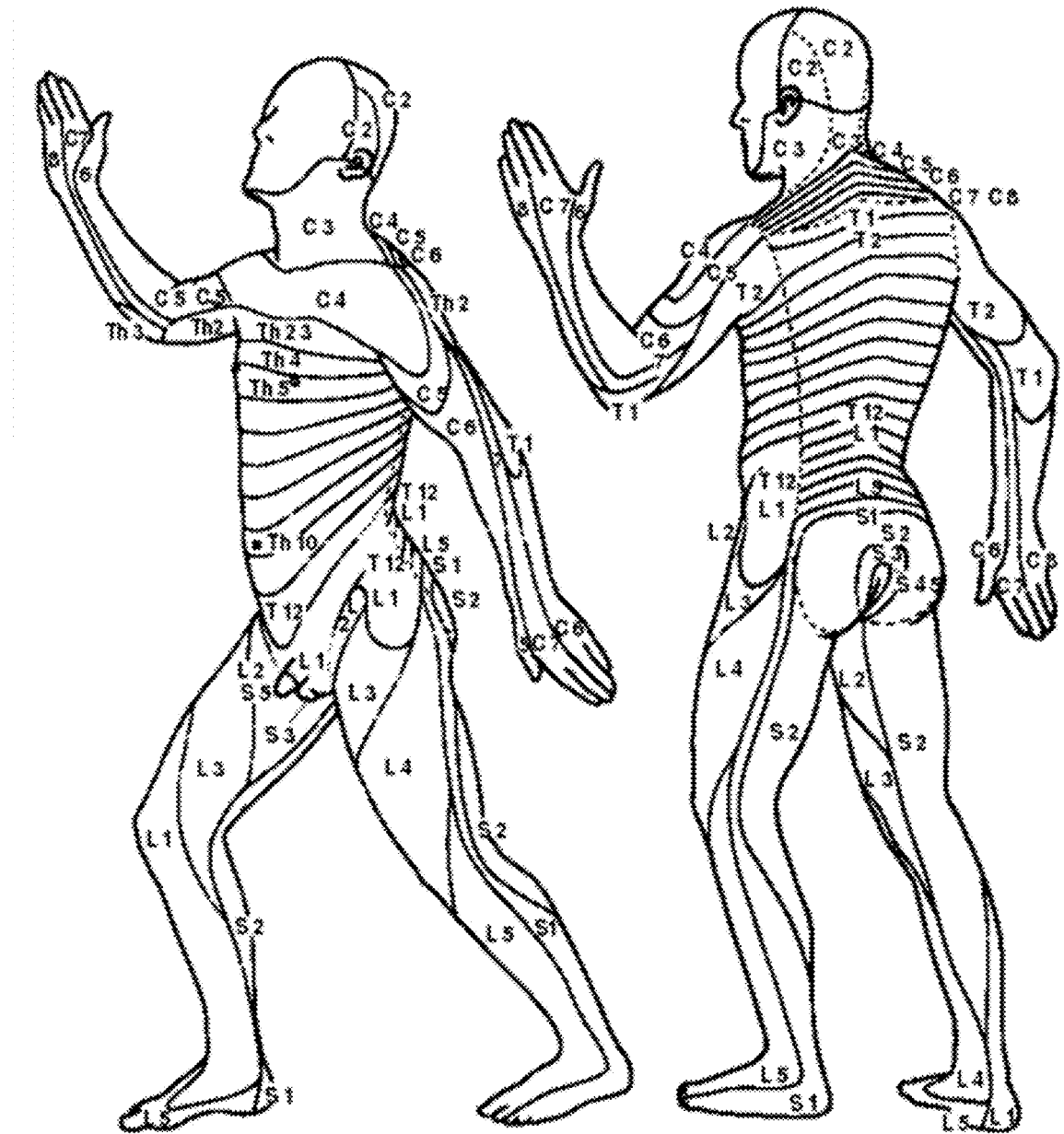
FIG. 4 depicts the various dermatome levels of vertebrae that correspond to the nerve distribution for a typical patient.

The neural stimulator device 210 may then be advanced gently through the epidural space 206 to the top vertebrae level for the pain-relief therapy to be administered to the proper dermatome level, as shown in FIG. 4. The neural stimulator device 210 may be inserted slowly through the introducer sheath 202 and advanced to the location with the highest probability of pain relief coverage. The location with the highest probability of pain relief coverage may be determined on-site as the location of neurostimulator placement when the patient feels that the sensation for pain relief, as a result of electric stimulation through electrodes 208 on the neurostimulator system 210, substantially covers a primary pain area of the patient.

Fluoroscopy, including X-ray and ultrasound, may be used to visualize the placement of the implantable neurostimulator. As discussed above, the neurostimulator system 210 may be passed through the interior lumen of the introducer sheath 202. The neurostimulator system 210 may be advanced through the epidural space 206 so that the electrodes 208 of the neurostimulator system 210 may be placed to target tissue in need of pain-relief. The size, form factor, and profile of the implantable neurostimulator system 210 allow the neurostimulator system 210 to be passed through introducers with inner lumen sizes as small as 28 Gauge. Coupled with local anesthesia, the patient is expected to provide feedback about the pain-relief therapy during a placement procedure. In particular, the patient may provide live feedback to the treating physician performing the procedure. For example, the patient may let the treating physician know whether a new placement of the neurostimulator system 210 gives rise to an improved sensation for pain relief. The improved sensation may include better area coverage or better pain-relief. The treating physician may adjust the placement of the neurostimulator system 210 according to the live feedback from the patient during the implantation procedure. The neurostimulator system's implantation position may be monitored in anterior-posterior and lateral views under fluoroscopy. The implantation location of the neurostimulator system 210, as noted by the patient and monitored by fluoroscopy during the implantation procedure, may be compared with the location of the highest probability of therapeutic paresthesia coverage. FIG. 4 depicts the various dermatome levels of vertebrae that correspond to the nerve distribution for a typical patient which would influence placement of the implanted neural stimulators in the spinal column.

Figure 2E:
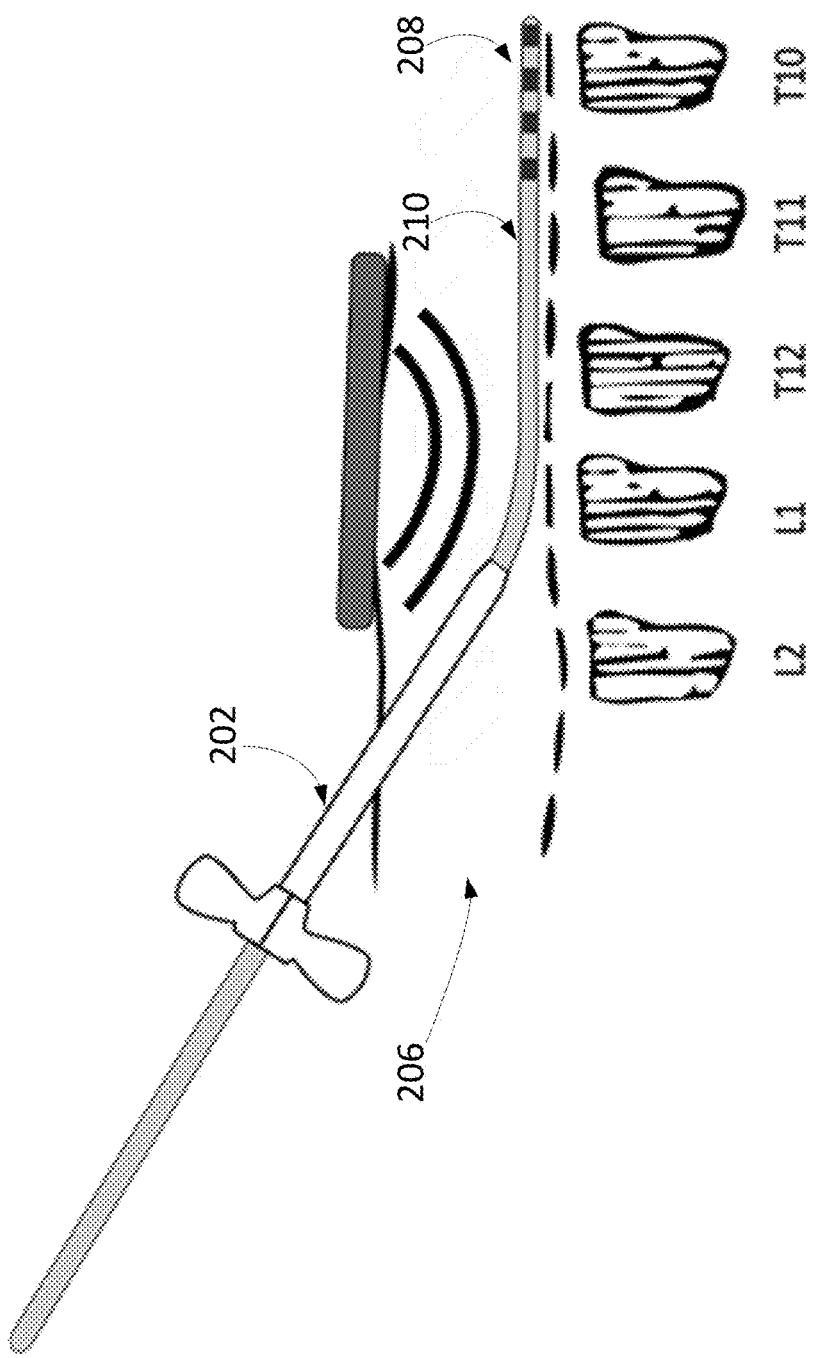
Figure 5A:
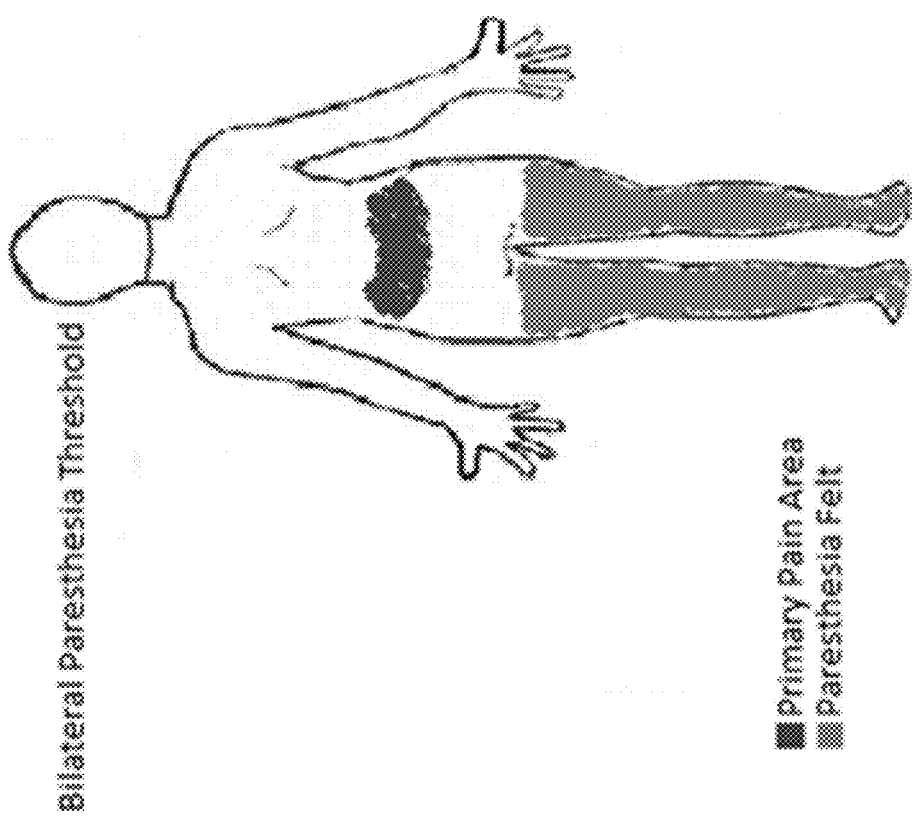
FIG. 5A and FIG. 5B show the respective stimulation areas mapped as an overlay on the painful regions in the lower portion of the body and the low back region of a typical patient.
Figure 5B:
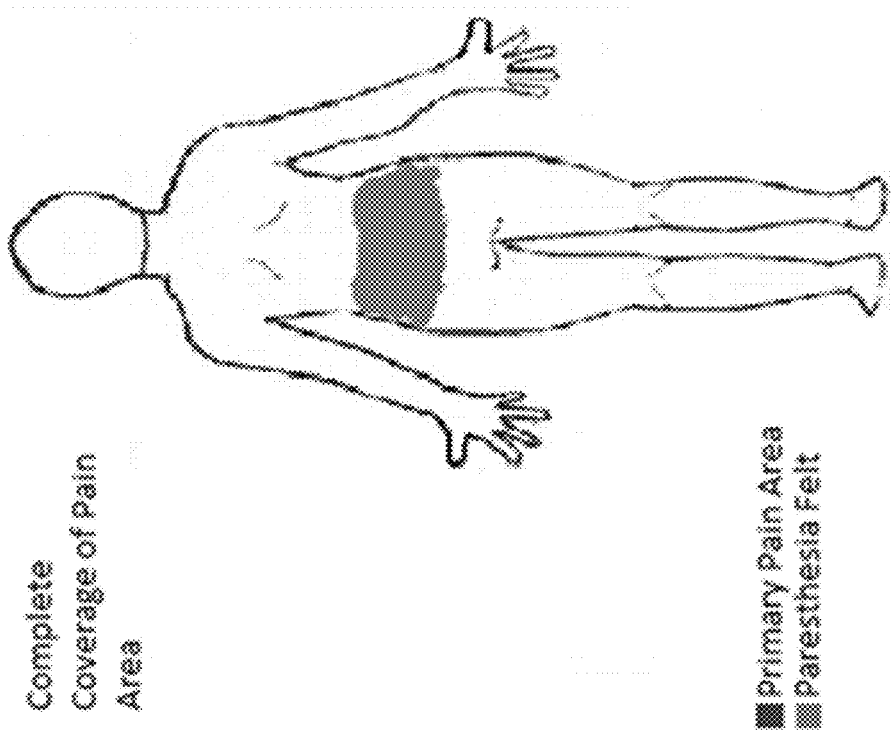

Returning to FIG. 2E, once the optimal implantation position has been determined based on the physiological dermatome mapping estimation, the treating physician may utilize a clinical position tester unit to provide remote power to the implanted device. The clinical position tester may include an external pulse generator. The external pulse generator may couple to receive antennas on the neurostimulator system through electric radiative coupling. The external pulse generator may provide electric power and excitation waveform parameters via the electric radiative coupling. During the implantation procedure, the treating physician may place the external pulse generator including a transmitter above the area of the implanted neurostimulator system, but not directly on the skin, as shown in FIG. 2E. The waveform parameters may include various settings of pulse width, pulse repetition rate, and power level etc. The waveform parameters can also include polarity setting information for each electrode on neurostimulator system 210. Electronic circuitry within the implantable neurostimulator system 210 may generate excitation waveforms, as prescribed by the waveform parameters and based on the electric energy received at the receive antennas, to drive the electrodes on the neurostimulator system. The electronic circuitry may also configure the polarity settings of the electrodes in accordance with the polarity setting information. Examples of the implantable electrodes, antenna, and circuits of the neurostimulator system 210 as well as the controller module can be found in PCT/US2012/50633, which is incorporated herein by reference. As noted above, the neurostimulator may be placed in close proximity to target tissues to receive pain-relief therapy. Referring to FIG. 5A, the area of pain is shown along with the area of paresthesia. In FIG. 5A, the area of paresthesia does not overlap with the primary area of pain and hence complete coverage of therapeutic relief may not be achieved. FIG. 5B, on the other hand, depicts the primary area of pain and paresthesia feeling in the same areas. Hence, FIG. 5B shows an adequate masking of the pain in which the area of paresthesia feeling substantially overlaps the primary area of pain where pain relief is sought.

The stimulation parameters utilized in the transmitter device may be programmed remotely through an encrypted Bluetooth® connection. A specialized iPad pre-loaded with the Programming Application may be utilized. Each transmitter has a unique identification number which will be listed as available devices in the software application. Once a device is selected, the connection password for that transmitter may be entered. Once the connection is made, and secured when the iPad identifies the device, the programmer and the transmitter are then considered paired. Once connected, the clinician can program the preset programs.

In order to test the nerve stimulation intraoperatively, the neurostimulator system may be held in place and the stylet may be completely withdrawn, as discussed above. The external antenna of the external pulse generator may be placed in a sterile drape or sterile fluoroscope bag over the region directly above the most proximal implanted electrode in the neurostimulator. To identify the most appropriate stimulation parameters, waveform parameters defining a medium pulse width and frequency range may be used in the beginning of testing. The pulse amplitude may be increased gradually while the patient, under local anesthesia, may be asked close-ended questions to identify the perception threshold, the discomfort threshold, and the area of paresthesia coverage, etc. Hence, the waveform parameters substantially optimized to provide pain relief therapy may be determined on site, during the implantation procedure. The determined waveform parameters may be entered into the preset programs for the patient to activate, for example, at home.

Figure 2F:
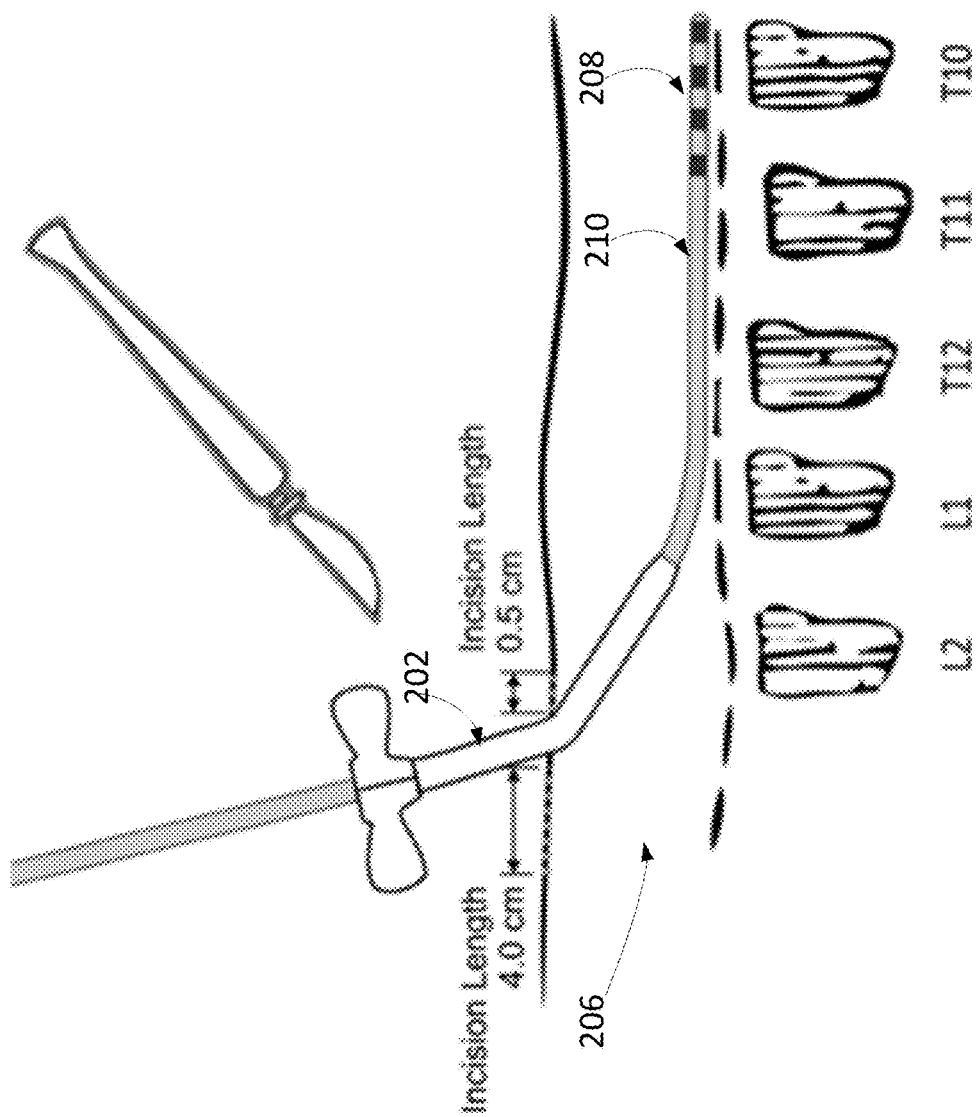

For context, FIG. 2F shows the recommended incision entry length for placement of an anchor to secure the neurostimulator body to tissue. As illustrated, the incision entry length may range from 0.5 cm to 4.5 cm to accommodate, for example, a reasonable slackness of neurostimulator body during implantation. In some implementations, two or more neurostimulator systems 210 may be placed. In some implementations, the second neurostimulator system 210 may be inserted into the inner lumen of the same introducer sheath. The second neurostimulator system 210 may be placed with the aid of a guide wire to clear the pathway in the epidural space 206, as described by the above steps; and the paresthesia coverage may be substantially optimized for both neurostimulator systems 210 in accordance with the disclosure herein.

In the patient's chart, the treating physician may document the neurostimulator position that provided appropriate stimulation coverage. The treating physician may record the stimulation settings and patient responses. The treating physician may also include a fluoroscopic image of the final implanted position of the neurostimulator system.

If a second neurostimulator system 210 is indicated, the steps shown in FIG. 2A to FIG. 2F may be repeated with additional considerations for placing the second neurostimulator system 210. The second neurostimulator system 210 may be placed parallel to the first neurostimulator system 210 and approximately 1 mm to 3 mm lateral to the physiological midline. The second neurostimulator system 210 may be typically placed one vertebrae level below the first neurostimulator system 210 bilaterally. This parallel placement can reduce the occurrences of nicking or cutting the first neurostimulator and to allow sufficient space for suturing both neurostimulator and anchors. The neurostimulator systems 210 are staggered so that the contacts are placed several vertebral spaces apart, depending on the position that corresponds to the most effective paresthesia.

Figure 2G:
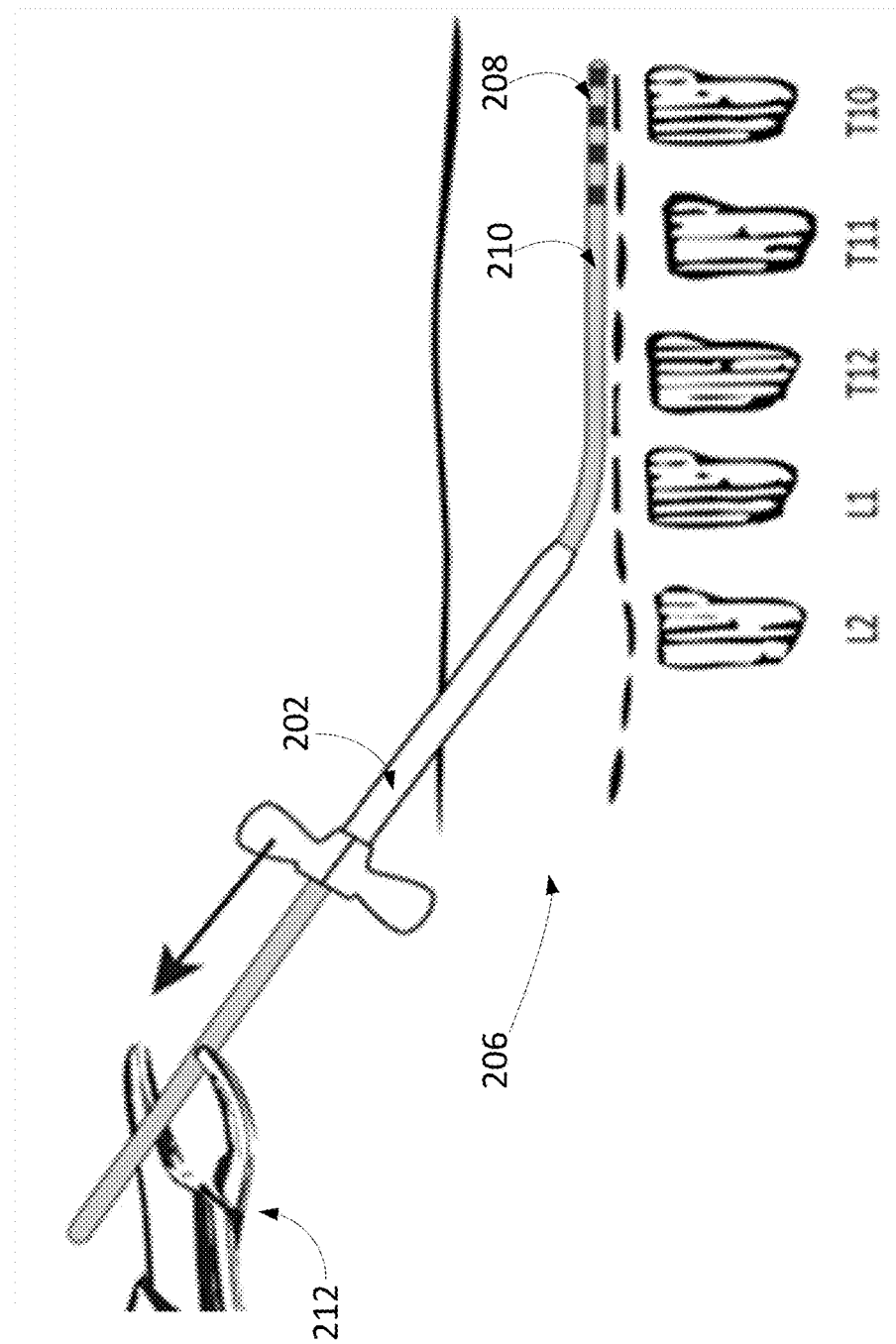

Once the proper location is confirmed and pain relief is achieved, the introducer sheath 202 may be removed from the tissue with forceps 212 to guide the introducer sheath 202 off of the neurostimulator body without disrupting the position of the neurostimulator system 210, as shown in FIG. 2G.

Figure 2H:
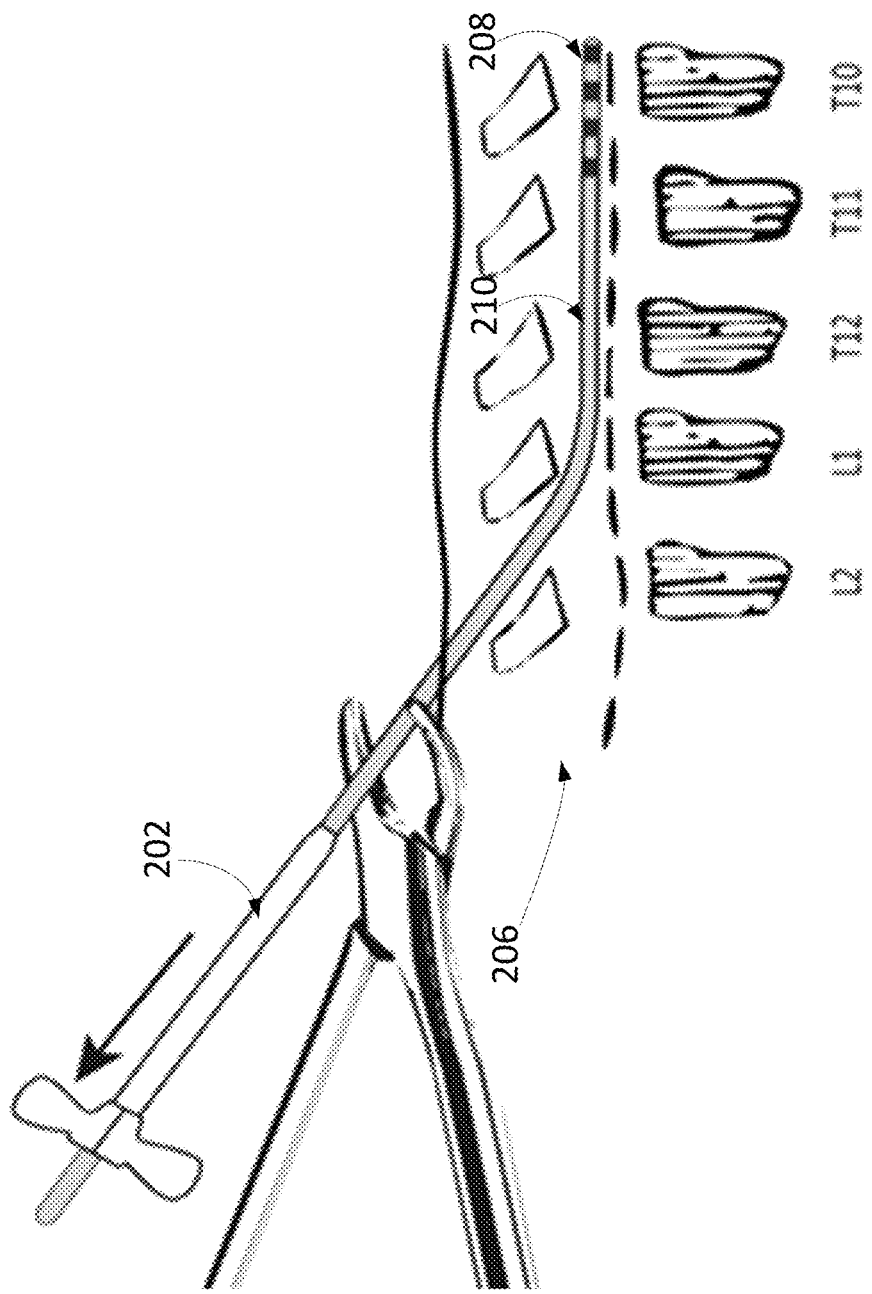

In order to facilitate the removal of the introducer sheath, a breakaway introducer sheath may be included in the device kit. The breakaway introducer sheath may be moved outside of the skin tissue into the exposed air, as shown in FIG. 2H. Once the breakaway introducer sheath has been moved outside of the skin tissue, the lead body tubing may be then cut to approximately 5 cm above the skin line, as illustrated by FIG. 2H. Notably, placement of the implantable neurostimulator system allows length adjustment of the neurostimulator body tubing on site during the procedure. Hence, the length of the implantable neurostimulator system 210 may be customized to a patient to provide substantially optimized coverage of pain-relief therapy. This is advantageous relative to implantable neurostimulators that are generally fixed in length and do not allow such on-site adjustment.

Figure 3A:
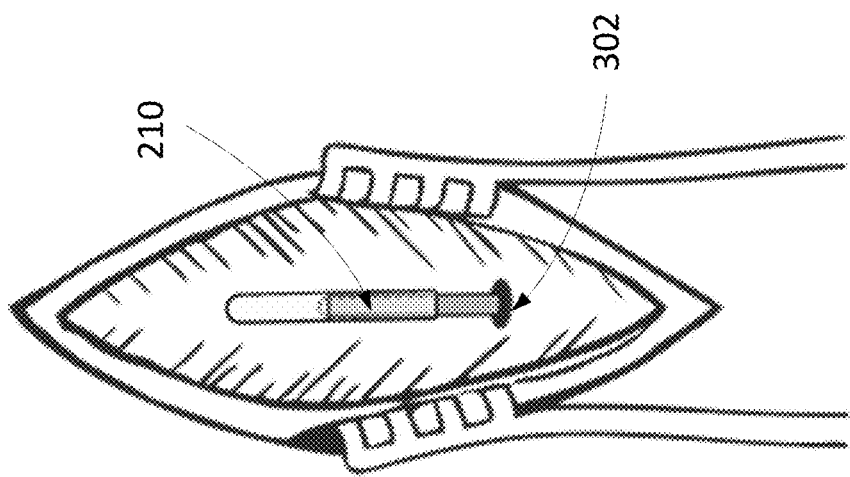
FIGS. 3A to 3B depict anchoring the implantable neural stimulator.
Figure 3B:
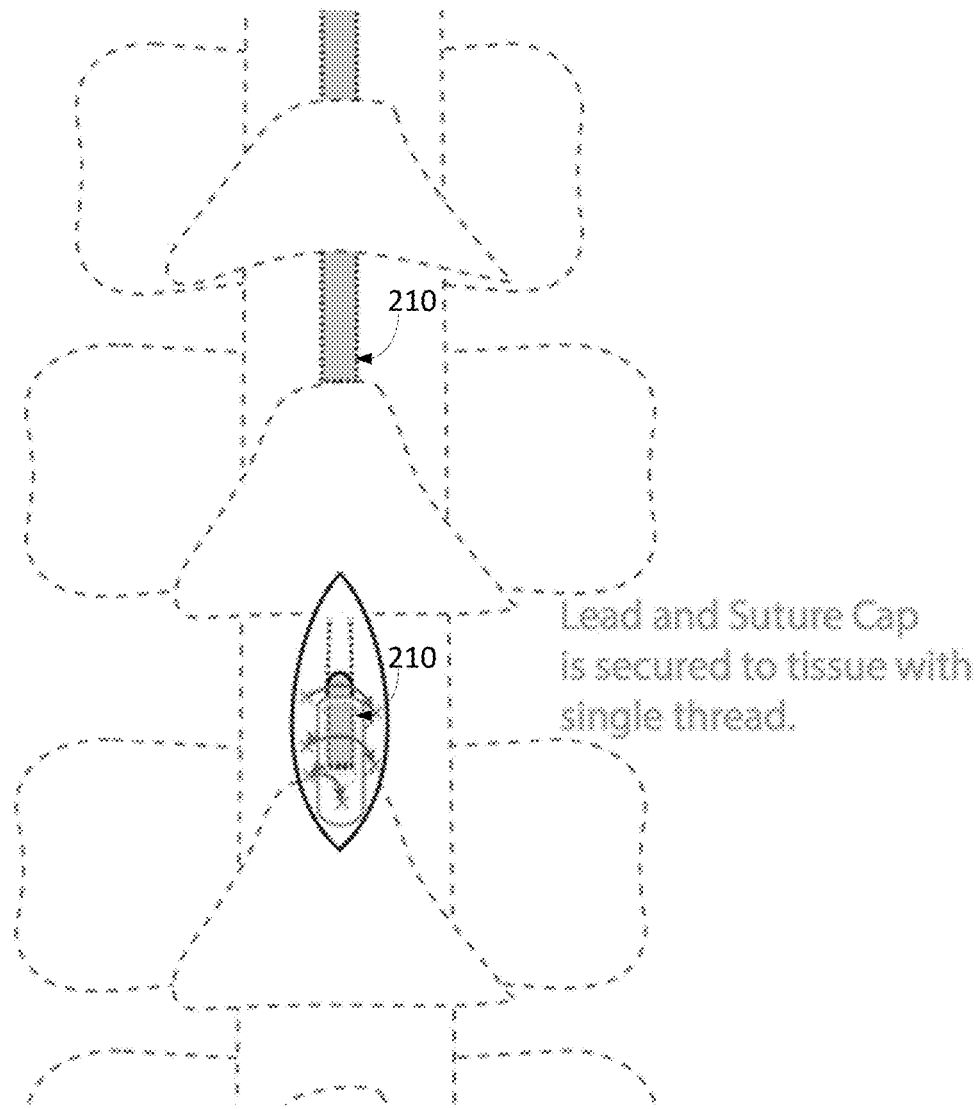

Anchoring may be the next step in the process. To prepare the anchor site, a longitudinal incision may be made around the introducer sheath shaft. FIGS. 3A to 3B show the placement of an anchor on the end of an implantable neurostimulator body to assist in suturing the neurostimulator to the fascia or to the ligamentum flavum. Dissection down to the supraspinous ligament may be conducted and hemostasis may be established, the position may expose the layers of tissue, as illustrated in FIG. 3A. While maintaining the neurostimulator position by placing light pressure on the proximal end, minimal force may be used to remove the introducer sheath. The neurostimulator system 210 may be held in place using flat, dull tweezers or forceps while removing the introducer sheath 202. Sterile scissors may be used to cut the excess device body length away from the implanted portion. At least 2 cm of device body may be maintained to allow for proper sleeve cap attachment. The excess device body length may be cut away. The sleeve cap may be connected onto the proximal end of the device and pushed gently down until the sleeve cap reaches the final position. A radio-opaque plug 302 may be mounted at the proximal tip, shown at 6 o'clock of the opening in FIG. 3A. The radio-opaque plug 302 may serve as a marker on radiographic images to locate the neurostimulator system 210. Care may be used to maintain the neurostimulator position.

The placement of an anchor on the end of the device body may assist in suturing the neurostimulator system 210 to the fascia or to the ligamentum flavum. FIG. 3A shows a 1.5 inch incision made and the clamps to pull back the skin to slip the sleeve cap on the end of the neurostimulator system 210 that has just been cut to size.

FIG. 3B shows the lead system 210 and the sleeve cap being secured to surrounding tissue with a single thread of suture. For example, a 2-0 non-absorbable suture can be used to secure the sleeve cap to the connective tissue, as shown in FIG. 3B. The device position may be confirmed to ensure that the neurostimulator system 210 has not moved by performing intraoperative stimulation to verify test stimulation parameters. If the neurostimulator system 210 has moved, the neurostimulator system 210 may be repositioned. Once the neurostimulator system 210 is confirmed to be in position, the incision may be closed using standard surgical techniques and dressings.

During home use, the transmitter of an external pulse generator may be placed over the region of the implanted neurostimulator in order for power to transfer. To do so, the transmitter is attached around the midsection of the patient with the antenna portion of the transmitter directly over the lower back overtop of a thin layer of clothing. The transmitter may not be placed directly on the skin. The patient may choose from three pre-programmed parameter setting combinations. Each combination may have a set rate and width provided by the clinician. The patient can change programs by pressing the A, B, or C buttons on the transmitter. If the stimulation is too strong, the amplitude can be decreased by pressing the decrease stimulation key. If the stimulation is not strong enough, the amplitude can be increased by pressing the increase stimulation key. If there is an unexpected change in stimulation, the transmitter should be immediately removed. If stimulation adjustment does not result in an effective setting, the clinician should be contacted. Examples of the implantable neural stimulator and controller module can be found in PCT/US2012/50633, which is incorporated herein by reference.

If it is determined that the neurostimulator system 210 needs to be explanted, the incision site from the original implantation procedure should be located. Fluoroscopy, including ultrasound and X-ray, can be used to visualize the location. As discussed above, a radiopaque marker 302 may be included in the suture sleeve cap. Additional radiopaque markers may include rings on the body of the neurostimulator, at a separation of, for example, every 2 cm. These radiopaque markers may manifest as dense objects on X-ray images to indicate the location of the implantable neurostimulator. The radiopaque markers may also manifest as echo-genic interfaces on an ultrasound image to provide locational guidance. Based on the locational information revealed from the radiopaque markers, the treating physician may make an incision to the depth of the proximal end of the device (also referred to as the "tail"). If applicable, the treating physician may cut sutures free of any tissue structures or scarring. The treating physician may remove the neurostimulator system 210 by slowly pulling on the proximal end. After the neurostimulator system 210 has been removed, the treating physician may verify that all components are intact and that all implanted materials are accounted for. The treating physician may then close the incision using standard surgical techniques and dressings.

Figure 6:
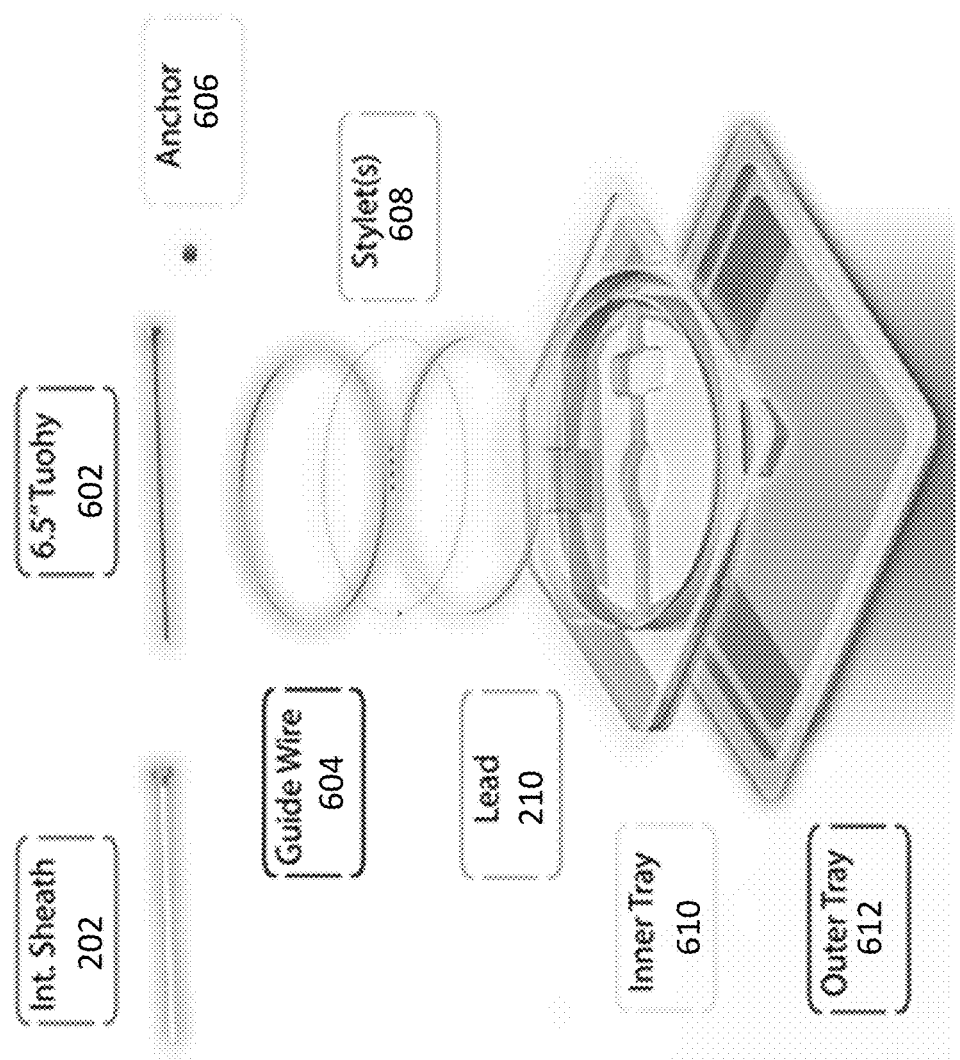
FIG. 6 depicts the elements of the neurostimulator kit package in an exploded view.

FIG. 6 shows the neurostimulator kit elements, unpacked and placed in the sterile field. The neurostimulator kit may include the guide wire 604, the Tuohy needle 602, the introducer sheath 202, the stylets 608, the neurostimulator system 210, and the anchor 606. As illustrated, the neurostimulator kit is packaged and enclosed by inner tray 610 and outer tray 612.

What is claim is:

1. A method for implanting a neurostimulator system, comprising:
    inserting an introducer sheath and a needle, carried by the introducer sheath, through an incision site on a patient and into an epidural space of the patient;
    withdrawing the needle through the introducer sheath and out of the patient;
    after withdrawing the needle out of the patient, inserting the neurostimulator system through the introducer sheath and into the epidural space of the patient, the neurostimulator system comprising an enclosure housing electrodes and at least one passive antenna, the at least one passive antenna configured to receive, via electric radiative coupling, electrical energy and waveform parameters from an antenna located exteriorly to the patient, and the electrodes configured to generate electrical waveforms from the electrical energy and the waveform parameters received at the at least one passive antenna;
    advancing the neurostimulator system through the epidural space until the electrodes are positioned adjacent a targeted tissue of the patient so that the electrodes can apply the electrical waveforms to render pain relief therapy to the targeted tissue and in a manner such that a proximal portion of the enclosure remains external to the patient;
    removing the introducer sheath from the epidural space of the patient;
    removing the proximal portion of the enclosure from the neurostimulator system to leave an implanted portion of the enclosure remaining in the epidural space such that the implanted portion of the enclosure has a customized length that is specific to the patient;

after removing the proximal portion of the enclosure, attaching a cap carrying a radiopaque marker to the implanted portion of the enclosure; and after attaching the cap to implanted portion of the enclosure, further attaching the cap to a connective tissue at the incision site to anchor the implanted portion of the enclosure to the patient.

2. The method of claim 1, wherein removing the proximal portion of the enclosure comprises cutting the enclosure such that the implanted portion, having the customized length, fits between the incision site on the patient and the targeted tissue of the patient.

3. The method of claim 1, further comprising: positioning the enclosure such that the pain relief therapy provided by the electrodes covers an area that substantially overlaps a primary pain area of the patient.

4. The method of claim 3, further comprising: adjusting the waveform parameters to improve the pain relief therapy provided by the electrodes of the neurostimulator system.

5. The method of claim 1, further comprising: inserting an additional neurostimulator system through the introducer sheath and into the epidural space of the patient, the additional neurostimulator system comprising an additional enclosure housing additional electrodes and at least one additional passive antenna, the at least one additional passive antenna configured to receive, via electric radiative coupling, electrical energy and waveform parameters from the antenna located exteriorly to the patient.

6. The method of claim 5, further comprising: advancing the additional neurostimulator system through the epidural space until the additional electrodes are located at a position that is spaced apart from the targeted tissue so that the additional electrodes can apply additional electrical waveforms to enhance the pain relief therapy.

7. The method of claim 5, further comprising: advancing the additional neurostimulator system through the epidural space until the additional electrodes are positioned near the targeted tissue of the patient so that the additional electrodes can apply additional electrical waveforms to the targeted tissue to enhance the pain relief therapy.

8. The method of claim 1, further comprising: using X-Ray fluoroscopy to guide movement of the neurostimulator system through the introducer sheath and into the epidural space.

9. The method of claim 1, further comprising: using X-Ray fluoroscopy to guide advancement of the neurostimulator system through the epidural space.

10. The method of claim 1, further comprising: using ultrasound sonography to guide movement of the neurostimulator system through the introducer sheath and into the epidural space.

11. The method of claim 1, further comprising: using ultrasound sonography to guide advancement of the neurostimulator system through the epidural space.

12. The method of claim 1, further comprising:

using fluoroscopy to locate the radiopaque marker before explanting the implanted portion of the enclosure that has been anchored to the patient.

13. The method of claim 1, further comprising:

using ultrasound sonography to locate the radiopaque marker before explanting the implanted portion of the enclosure that has been anchored to the patient.

14. The method of claim 1, further comprising: inserting a guide wire through the introducer sheath and advancing the guide wire into the epidural space.

15. The method of claim 14, further comprising: advancing the guide wire to no more than approximately 3 cm past a tip of the introducer sheath.

16. The method of claim 15, further comprising: advancing the neurostimulator system by gliding the neurostimulator system within the introducer sheath and into the epidural space.

17. The method of claim 1, wherein anchoring the implanted portion of the enclosure comprises suturing the cap to the connective tissue at the incision site.

18. The method of claim 1, wherein the implanted portion of the enclosure extends from a first end that is lateral to the midline of the patient and adjacent the targeted tissue to a second end that is under the incision site without pointing to the incision site through which the introducer sheath was placed.

19. The method of claim 1, wherein the needle is configured to block the electrical energy from the antenna located exteriorly to the patient.

20. The method of claim 1, wherein the implanted portion of the enclosure has a length of at least 2 cm for accommodating the cap.

21. The method of claim 1, wherein the incision site has a length in a range of 0.5 cm to 4.5 cm for allowing passage of the introducer sheath.

* * * * *